United States Patent
Vogt et al.

(10) Patent No.: US 6,942,877 B2
(45) Date of Patent: Sep. 13, 2005

(54) METHOD FOR PRODUCING ANTIBIOTIC COMPOSITES

(75) Inventors: Sebastian Vogt, Jena (DE); Matthias Schnabelrauch, Jena (DE); Klaus-Dieter Kühn, Marburg (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 296 days.

(21) Appl. No.: 10/100,843

(22) Filed: Mar. 19, 2002

(65) Prior Publication Data

US 2002/0192279 A1 Dec. 19, 2002

(30) Foreign Application Priority Data

Mar. 22, 2001 (DE) .......................... 101 14 364

(51) Int. Cl.⁷ .................. A61F 13/00; A61F 2/00; A61K 9/14; A61K 9/50
(52) U.S. Cl. .................. 424/489; 424/422; 424/423; 424/424; 424/484; 424/486; 424/501; 424/675; 424/682
(58) Field of Search ................. 424/484, 486, 424/489, 501, 422, 423, 424, 675, 682

(56) References Cited

U.S. PATENT DOCUMENTS

| | | | |
|---|---|---|---|
| 3,022,286 A | 2/1962 | Van de Griendt | 260/210 |
| 3,091,572 A | 5/1963 | Luedemann et al. | 167/65 |
| 3,536,759 A | 10/1970 | Jurado et al. | 260/559 |
| 3,882,858 A | 5/1975 | Klemm | 128/92 G |
| 4,059,684 A | 11/1977 | Gross et al. | 424/4 |
| 4,191,740 A | 3/1980 | Heusser et al. | 424/14 |
| 4,233,287 A | 11/1980 | Heusser et al. | 424/14 |
| 4,291,013 A | 9/1981 | Wahlig et al. | 424/16 |
| 4,440,661 A * | 4/1984 | Takeuchi et al. | 510/438 |
| 4,617,293 A | 10/1986 | Wahlig et al. | 514/41 |
| 5,607,685 A | 3/1997 | Cimbollek | 424/422 |
| 5,670,142 A | 9/1997 | Rubin | 414/78.05 |
| 5,807,567 A | 9/1998 | Randolph et al. | 424/426 |
| 5,874,418 A * | 2/1999 | Stella et al. | 514/58 |
| 6,077,822 A | 6/2000 | Dyrsting | 514/8 |
| 6,485,754 B1 * | 11/2002 | Wenz et al. | 424/602 |

FOREIGN PATENT DOCUMENTS

| | | |
|---|---|---|
| BE | 821 600 | 2/1975 |
| DE | 32 48 328 A1 | 6/1984 |
| DE | 0115001 | 8/1984 |
| ES | 354173 | 10/1970 |
| GB | 1 046 332 | 10/1966 |
| GB | 1 478 240 | 6/1977 |
| NL | 660 9490 | 1/1967 |
| WO | 9527517 | 10/1995 |

OTHER PUBLICATIONS

Abstract—ES 3309402; Conrado Folch Vazquez, "Tetracycline lauryl sulfate", Feb. 8, 1996.
Abstract—ES 322771; Conrado Folch Vazquez, "Tetracycline lauryl sulfate", Feb. 8, 1996.
Abstract of EP 0115001 from EPO website database.
Abstract of WO 9527517 from EPO website database.

* cited by examiner

*Primary Examiner*—Thurman K. Page
*Assistant Examiner*—S. Tran
(74) *Attorney, Agent, or Firm*—Norris McLaughlin & Marcus PA

(57) ABSTRACT

A method for producing antibiotic composites is described, which is characterized in that a salt, which can be subjected to plastic deformation and which consists of at least one cationic component of a protonated antibiotics base from the groups of aminoglycoside antibiotics, the lincosamide antibiotics and the tetracycline antibiotics and of at least one anionic components from the group of organic sulfates and/or organic sulfonates and/or fatty acid esters, is used as a binding agent for the fixation of inorganic composite components and/or possibly organic composite components and possibly for the molding of the composites while adding water, especially through pressing, extrusion, rolling, calendering and grinding processes.

21 Claims, No Drawings

METHOD FOR PRODUCING ANTIBIOTIC COMPOSITES

The present invention relates to a method for producing antibiotic composites, which can be used as implants in human and veterinary medicine for treating local microbial infections in hard and soft tissues.

It has been long known that a systemic application of antibiotics is associated with a number of problems. The systemic application often makes it necessary to use very high antibiotics dosages in order to be able to achieve antimicrobially effective antibiotics concentrations in the infected tissue. Especially with aminoglycoside antibiotics and tetracycline antibiotics, this can lead to severe injury of the organism due to their nephrotoxic and ototoxic character. Therefore the idea of using antibiotics in locally applicable release systems and/or converting them into suitable delivery forms has been pursued for decades. For the treatment of local microbial infections of soft and hard tissues in human and veterinary medicine, it is particularly important that after the initially high antibiotics dosage, a release of lower antibiotics quantities over a period of days up to several weeks is ensured in order to achieve the largest possible elimination of microorganisms. This is of critical importance especially for infections of the bone tissue to be able to fight the infection successfully. Of particular interest in this context are such composites that, apart from an antibiotic effect, also exhibit osteoconductive effectiveness due to their chemical composition and structure.

For the medical application of antibiotic delivery systems it is necessary to formulate the appropriate antibiotics into pharmaceuticals or implants that can be easily handled and stored Through the use of suitable adjuvants. These pharmaceuticals and implants represent composite systems consisting of the respective active substance and the adjuvant that is necessary for the formulation.

These formulations can assume a liquid or solid state. Solid states of matter in the form of molded bodies, tablets, granules and powders require sufficient mechanical stability. To accomplish this it is necessary to combine the active substance and the adjuvants with each other in a mechanically stable fashion. This can occur on one hand through chemical curing processes of the adjuvants and on the other hand through pressing processes for adjuvants that can be subjected to plastic deformation and form a composite under pressure.

Antibiotic deposit systems for the treatment of local infections are the object of a variety of publications and patents, to which reference can be made here only in a limited number to serve as examples.

The physical fixation of antibiotics while using non-resorbable polymers was the content of a series of patents, of which only a few are listed here. For example Klemm (K. Klemm: Surgical synthetic-resin material and method of treating osteomyelitis, May 13, 1975, U.S. Pat. No. 3,882, 858) suggests treating osteomyelitis with plastic particles made of polymethacrylate, polyacrylate as well as their copolymers, which have been impregnated with gentamicin or other antibiotics. Klemm describes the usage of septopal (K. Klemm: Septopal—a new ay of local antibiotic therapy; in T. J. G. Van Rens, F. H. Kayser (Eds.), Local antibiotic Treatment in Osteomyelitis and Soft-Tissue Infections, Excerpta Medica, Amsterdam (1981) 24–31; K. Klemm: Antibiotic beat chains. Clin. Orthop. Relat. Res. 295 (1993) 63–76). The description involves commercially available gentamicin-releasing chains of polymethacrylate. Heuser and Dingeldein describe a composition on the basis of antibiotics and polymethymethacrylate or polyacrylate, to which amino acids have been introduced as an added component (D. Heuser, E. Dingeldein: Synthetic resin-base, antibiotic compositions containing amino acids, Apr. 04, 1980, U.S. Pat. No. 4,191,740; D. Heuser, E. Dingeldein: Synthetic resin-base, antibiotic compositions containing amino acids, Nov. 11, 1980, U.S. Pat. No. 4,233,287). Furthermore antibiotics, particularly aminoglycoside antibiotics, were also integrated in bone cement (A. Gross, R. Schaefer, S. Reiss: Bone cement compositions containing gentamicin, Nov. 22, 1977, U.S. Pat. No. 4,059,684; A. Welch: Antibiotics in acrylic bone cement. In vitro studies. J. Biomed. Mater. Res. 12 (1978) 679; R. A. Elson, A. E. Jephott, D. B. McGechie, D. Vereitas: Antibiotic-loaded acrylic cement. J. Bone Joint Surg. 59B (1977) 200–205). The binding agents used in this process were the polymers that are created during hardening of the cement.

The formation of antibiotics deposits with the help of resorbable polymers, especially of polyesters of the (α-hydroxy carboxylic acids, was also the object of a series of publications, which are also referenced here only to a limited extent to serve as examples. Sampath et al. suggest a gentamicin-releasing system, consisting of poly-L-lactide and gentamicin, which was produced by pressing together poly-L-lactide/gentamicin microcapsules (S. S. Sampath, K. Garvin, D. H. Robinson: Preparation and characterization of biodegradable poly(L-lactic acid) gentamicin delivery systems. Int. J. Pharmaceutics 78 (1992) 165–174). This system reveals quite a significant delay in the release of the active substance, in dependency upon the gentamicin quantity that is used. In a similar system, poly-D,L-lactide was used for the production of micro spheres containing active substances (R. Bodmeier, J. W. McGinity: The preparation and evaluation of drug-containing poly(D,L-lactide) microspheres formed by solvent evaporation method. Pharm.: Res. 4 (1987) 465–471). Friess and Schlapp also describe microparticles made of polylactide, which are coated with collagen/gentamicin sulfate (W. Friess, M. Schlapp: Advanced implants for local delivery of gentamicin. Sixth World Biomaterials Congress Transactions (2000) 1488). These coated microspheres have only a very low tendency for delaying the release of gentamicin. Schmidt et al. suggested resorbable molded bodies containing gentamicin (C. Schmidt, R. Wenz, B. Nies, F. Moll: Antibiotic in vivo/in vitro release, histocompatibility and biodegradation of gentamicin implants based on lactic acid polymers and copolymers. J. Control. Release 37 (1995) 83–94). These products were manufactured by pressing together mixtures of gentamycin-sulfate/poly-L-lactide, gentamycin-sulfate/poly-D,L-lactide and gentamicin-sulfate/poly-D,L-lactide-coglycolide. These delivery preparations released about ninety percent of the antibiotic within 24 hours.

Apart from polymer-based systems also a number of inorganic systems with retarding effect have been described. The following references only a few systems made with calcium sulfate. Randolph et al. for example describes a retarding system, which is based on the inclusion of active substances in a calcium sulfate matrix (D. A. Randolph, J. L. Negri, T. R. Devine, S. Gitelis: Calcium sulfate controlled release matrix, Sep. 15, 1998, U.S. Pat. No. 5,807,567). These calcium sulfate pellets are produced from a mixture of α-calcium sulfate hemihydrate, α-calcium sulfate hemihydrate, an additive and water. Hardening takes place through the formation of calcium sulfate dihydrate. Turner et al. describe tablets made of calcium sulfate that contain tobramycin and are supposed to be used for treating medullary defects (T. M. Turner, R. M. Urban, S. Gitelis, A. M.

Lawrence-Smith, D. J. Hall: Delivery of tobramycin using calcium sulfate tablets to graft a large medullary defect: Local and systemic effects. Sixth World Biomaterials Congress Transactions (2000) 767). Similar delivery systems made of calcium sulfate, but with amikacin sulfate, are also described (D. W. Peterson, W. O. Haggard, L. H. Morris, K. C. Richelsoph, J. E. Parr: Elution of amikacin from calcium sulfate pellets: An in vitro study. Sixth World Biomaterials Congress Transactions (2000) 767).

So far sparingly soluble salts of the aminoglycoside antibiotics and the lincosamide antibiotics were little recognized in the production of deposit preparations. The formation of sparingly soluble salts or chelates of the tetracycline antibiotics has been general knowledge for decades. Folch Vazquez for example describes the production of tetracycline dodecyl sulfate through the conversion of tetracycline hydrochloride with sodium dodecyl sulfate in water (C. Folch Vazquez: Tetracycline lauryl sulfate, Feb. 08, 1966, ES 3 309 402; C. Folch Vazquez: Tetracycline derivatives, Jan. 09, 1967, NL 6609490). Alternatively the preparation can also occur from tetracycline and dodecyl sulphuric acid (C. Folch Vazquez: Tetracycline lauryl sulfate, Feb. 08, 1966, ES 322 771). Furthermore, the usage of tetracycline sulfamates for antibiotic therapy was suggested (A. Jurando, J. M. Puigmarti: Antibiotic tetracycline sulfamate and its derivatives, Oct. 27, 1970, U.S. Pat. No. 3,536,759; Anonymous: Antibiotic tetracycline alkyl sulfamates, Oct. 16, 1969, ES 354 173; C. Ciuro, A. Jurado: Stability of a tetracycline derivative. Afinidad 28 (292) 1971, 1333–5). Among the aminoglycoside antibiotics, a series of hardly soluble salts is also basically known. For gentamicin, for example, the presentation of scarcely soluble salts based on higher fatty acids, aryl alkyl carboxylic acids, alkyl sulfates and alkyl sulfonates was described (G. M. Luedemann, M. J. Weinstein: Gentamycin and method of production, Jul. 16, 1962, U.S. Pat. No. 3,091,572). Examples of this are gentamicin salts of lauric acid, stearic acid, palmitic acid, oleic acid, phenyl butyric acid, naphthalene-1-carboxylic acid, lauryl sulphuric acid and dodecyl benzene sulphonic acid. These salts frequently proved to be disadvantageous because they represent resinous, hydrophobic substances, which prevent galenical usage. Nevertheless, fatty acid salts of gentamicin and etamycin were synthesized from the free base or its salts in water at 50–800 C (H. Voege, P. Stadler, H. J. Zeiler, S. Samaan, K. G. Metzger: Sparingly-soluble salts of aminoglycosides and formations containing them with inhibited substance-release, Dec. 28, 1982, DE 3 248 328). These antibiotics fatty acid salts are supposed to be suitable as injection preparations. The production of gentamicin dodecyl sulfate and its use in ointments and creams was also described (C. Folch Vasquez: Gentamicin derivates, Oct. 29, 1974, BE 821 600). A newer development is presented with the hardly soluble aminoglycoside flavonoid phosphates (H. Wahlig, E. Dingeldein, R. Kirchlechner, D. Orth, W. Rogalski: Flavonoid phosphate salts of aminoglycoside antibiotics, Oct. 13, 1986, U.S. Pat. No. 4,617,293). The salts of phosphoric acid half esters from the derivatives of hydroxy flavanes, hydroxy flavenes, hydroxy flavanones, hydroxy flavones and hydroxy flavylium are described. Particularly preferred are the derivatives of the flavanones and the flavones. These hardly soluble salts should be used in deposit preparations. These salts were introduced for example into collagen shaped mass (H. Wahlig, E. Dingeldein, D. Braun: Medicinally useful, shaped mass of collagen resorbable in the body, Sep. 22, 1981, U.S. Pat. No. 4,291,013). Furthermore, artificial heart valves were impregnated with these sparingly soluble gentamicin salts, gentamicin crobefate (M. Cimbollek, B. Nies, R. Wenz, J. Kreuter: Antibiotic-impregnated heart valve sewing rings for treatment and prophylaxis of bacterial endocarditis. Antimicrob. Agents Chemother. 40(6) (1996) 1432–1437). The interesting aspect of this publication is in particular that a mixture of easily soluble gentamicin sulfate and sparingly soluble gentamycin crobefate is used. The objective with this was on one hand to achieve a high initial gentamicin concentration through the easily soluble gentamicin sulfate following introduction of the heart valve rings into the organism or into a model liquid, and on the other hand to enable a release of gentamycin over an extended period of time through the relatively insoluble gentamicin crobefate.

The present invention is based on the objective of developing a method for producing antibiotic composites that permits simple inexpensive production of composites without requiring inorganic or organic, non-antibiotic binding agents. These antibiotic composites should be able to be used as implants in human and veterinary medicine for treating local microbial infections in bone and soft tissues. Furthermore, the method that is supposed to be developed should be able to be applied not only for a particular antibiotic, but rather should be suitable for a number of antibiotics of similar structure.

The invention is based on the surprising finding that familiar organic sulfates, organic sulfonates and aliphatic carboxylates of the aminoglycoside, lincosamide and tetracycline types of antibiotics, which generally represent hydrophobic, resinous substances, can be subjected to plastic deformation and have binding agent properties. It turned out that these salts, which can be subjected to plastic deformation, form strong composites with adjuvants under pressure. This makes it possible to use these antibiotics salts as binding agents in the production of antibiotic composites from inorganic materials and possibly organic materials. Additional binding agents to ensure form stability of the composite are no longer required. In this way, costs can be saved, and there are no possible problems with biocompatibility and resorbability of additional inorganic and/or organic binding agents. The particular advantage of the invented binding agent for producing antibiotic composites, which are intended to be used for local infection control, is that after introducing the invented composite in an aqueous environment, the binding agent dissolves while releasing antibiotics, wherein a simultaneous decomposition of the composite occurs the more the binding agent dissolves. This means that with the increasing release of the antibiotics, the decomposition of the composite also increases.

The invention furthermore is based on the surprising finding that familiar organic sulfates and organic sulfonates of the aminoglycoside, lincosamide and tetracycline types of antibiotics are formed in the presence of inorganic composite components and possibly organic composite components through the action of water during the molding process of the molded body from conventional, water-soluble forms of antibiotics salts, such as the sulfates, through the conversion of water-soluble organic sulfates and sulfonates. This in situ formation of salts that can be subjected to plastic deformation makes a separate synthesis of the salts no longer necessary. This way cost-intensive synthesis and cleaning steps can be eliminated.

According to the invention, a salt, which can be subjected to plastic deformation and which consists of at least one cationic component of a protonated antibiotics base from the groups of aminoglycoside antibiotics, the lincosamide antibiotics and the tetracycline antibiotics and of at least one anionic components of the group of aliphatic carboxylates, alkyl sulfates, aryl sulfates, alkyl aryl sulfates, cycloalkyl sulfates, alkyl cycloalkyl sulfates, alkyl sulfamates, cycloalkyl sulfamates, alkyl cycloalkyl sulfamates, aryl sulfamates, alkyl aryl sulfamates, alkyl sulfonates, fatty acid-2-sulfonates, aryl sulfonates, alkyl aryl sulfonates, cycloalkyl sulfonates, alkyl cycloalkyl sulfonates, alkyl-di-sulfates, cycloalkyl disulfates, alkyl disulfonates, cycloalkyl disulfonates, aryl disulfonates, alkyl aryl disulfonates, aryl trisulfonates and alkyl aryl trisulfonates, is used as a binding agent for the fixation of inorganic composite components and/or possibly organic composite components and possibly for the molding of the composite while adding water, especially through pressing, extrusion, rolling, calendering and grinding processes.

The subsequent embodiments have been proven in practice.

Furthermore it is in accordance with the invention that from the group of alkyl sulfates especially dodecyl sulfate, tetradecyl sulfate, hexadecyl sulfate, octadecyl sulfonate and docosanol sulfate are used as the anionic component.

According to the invention, from the group of alkyl sulfonates, dodecyl sulfonate, hexadecyl sulfonate and octadecyl sulfonate are preferred as the anionic component.

It is also in accordance with the invention that aliphatic carboxylates, which contain 12 to 30 carbon atoms, are used as anionic components.

It is in accordance with the invention that from the group of aliphatic carboxylates palmitate, stearate and behenylate are used as anionic components.

According to the invention, the salt, which can be subjected to a plastic deformation, is synthesized before the molding process.

According to the invention, the salt, which can be subjected to plastic deformation, is formed during the molding process of the composite while introducing water into a mixture consisting of inorganic composite components, possibly organic composite components, one or more representatives from the aminoglycoside antibiotics and/or the lincosamide antibiotics and/or the tetracycline antibiotics, which exist in sulfate form, hydrochloride form, hydrobromide form and phosphate form, and one or more representatives from the alkyl sulfates, aryl sulfates, alkyl aryl sulfates, cycloalkyl sulfates, alkyl cycloalkyl sulfates, alkyl sulfamates, cycloalkyl sulfamates, alkyl cycloalkyl sulfamates, aryl sulfamates, alkyl aryl sulfamates, alkyl sulfonates, fatty acid-2-sulfonates, aryl sulfonates, alkyl aryl sulfonates, cycloalkyl sulfonates, alkyl cycloalkyl sulfonates, alkyl-disulfates, cycloalkyl disulfates, alkyl disulfonates, cycloalkyl disulfonates, aryl disulfonates, alkyl aryl disulfonates, aryl trisulfonates and alkyl aryl trisulfonates, which exist in sodium salt form and/or potassium salt form and/or in ammonium salt form and/or trialkyl ammonium salt form and/or in dialkyl ammonium salt form and/or in monoalkyl ammonium salt form and/or in triaryl ammonium salt form and/or in diaryl ammonium salt form and/or in aryl ammonium salt form and/or in alkyl diaryl ammonium salt form and/or in dialkyl aryl ammonium salt form and/or in tricycloalkyl ammonium salt form and/or in dicycloalkyl ammonium salt form and/or in monocycloalkyl ammonium salt form and/or in alkyl dicycloalkyl ammonium salt form and/or in dialkyl cycloalkyl ammonium salt form.

According to the invention, the alkyl sulfates, aryl sulfates, alkyl aryl sulfates, cycloalkyl sulfates and alkyl cycloalkyl sulfates are sulphuric acid half esters.

It is also in accordance with the invention that sodium dodecyl sulfate, sodium tetradecyl sulfate, sodium hexadecyl sulfate and sodium octadecyl sulfate are preferred as alkyl sulfates.

According to the invention, especially sodium dodecyl sulfonate, sodium hexadecyl sulfonate and sodium octadecyl sulfonate are preferred as alkyl sulfonates.

Furthermore it is in accordance with the invention that especially sodium dodecyl benzyl sulfonate is preferred as alkyl aryl sulfonate.

According to the invention, allomycin, amicetin, amikacin, apramycin, bekanamycin, betamicin, butirosin, destomyicn, dibekacin, dihydrostreptomycin, flambamycin, fortimycin A, fortimycin B, framycetin, gentamicin, hikizimycin, homomycin, hybrimycin, hygromycin B, kanamycin, kasuhamycin, lividomycin, minosaminomycin, neomycin, netilmicin, paromomycin, parvulomycin, puromycin A, ribostamycin, rimocidin, ristosamine, ristomycin, sagamycin, sisomicin, sorbistin, spectinomycin, streptomycin, tobramycin, tunicamycin, verdamycin from the group of aminoglycoside antibiotics are preferred.

According to the invention, clindamycin and lincomycin from the group of lincosamide antibiotics are preferred.

According to the invention, tetracycline, chlorotetracycline, oxytetracycline, demethylchlorotetracycline, methacycline, doxycycline, rolitetracycline and minocycline from the group of tetracycline antibiotics are preferred.

It is also in accordance with the invention that calcium carbonate, magnesium carbonate, calcium hydroxide, magnesium hydroxide, magnesium oxide, calcium sulfate, calcium sulfate hemihydrate, calcium sulfate dihydrate, tricalcium phosphate, tetracalcium phospate, calcium hydrogen phosphate, calcium hydrogen phosphate dihydrate, hydroxylapatite, fluorapatite, resorbable glass, resorbable glass ceramics and their blends are used as inorganic composite components.

Furthermore it is in accordance with the invention that the inorganic composite components are used in the form of powders and/or granulates.

Furthermore it is in accordance with the invention that preferably starch, cellulose, chitin, chitosan, gelatine, collagen, polymethacrylic acid ester, polyacrylic acid ester, polyvinyl alcohol, polyvinyl chloride, polyvinylidene chloride and polytetrafluorethylene and their blends are used as organic composite components.

According to the invention, easily water-soluble antibiotics are used as organic composite components.

Also according to the invention, the percentage by mass of salt that can be subjected to plastic deformation in the composites is between 0.1 and 98 percent by mass.

According to the invention, the composite is shaped into molded bodies, granulates and powders.

According to the invention, the composite can be subjected to plastic deformation.

It is also in accordance with the invention that the composite in the form of pastes is preferred. This makes it possible to knead the composite and mold it into infected hard tissue defects.

It is also in accordance with the invention that the composites are applied onto resorbable implants and non-resorbable implants as coatings.

The object of the invention will be explained in more detail with the following examples 1 and 2.

Manufacture of Antibiotics Preparations

EXAMPLE 1

A mixture of 25 mg gentamycin sulfate (700 U/mg, Fluka), 50 mg gentamycin pentakis dodecyl sulfate and 1,425 mg calcium sulfate dihydrate (Fluka) is prepared in a grinding process. 200 mg of this mixture are pressed in each case in a press at a pressure of 5 tons into disk-like, stable molded bodies with a diameter inside of 13 mm within two minutes.

EXAMPLE 2

A Mixture of 25 mg gentamycin sulfate (700 U/mg, Fluka), 48 mg gentamycin pentakis dodecyl sulfonate and 1,427 mg calcium hydrogen phosphate (Fluka) is prepared in a grinding process. 200 mg of this mixture are pressed in any given case in a press at a pressure of 5 tons into disk-like, stable molded bodies with a diameter of 13 mm within two minutes.

Antibiotics Delivery Experiments

The molded bodies produced in examples 1 and 2 were introduced into physiological saline and stored in said saline at 370° C. over a period of twelve days in order to determine the retarded release of antibiotics. Sampling occurred after 1, 3, 6, 9 and 12 days of storage time. Determination of the antibiotics value was conducted with an agar diffusion test while employing Bacillus subtilis ATCC 6633 as the test germ (for results please refer to Table 1).

TABLE 1

Cumulative Gentamicin Release from Sample Bodies of Examples 1 and 2 as a function of the Storage Time in Physiological Saline at 37° C.

| | Cumulative Gentamycin Release [Ma %] Storage Time [d] | | | | |
|---|---|---|---|---|---|
| Example | 1 | 3 | 6 | 9 | 12 |
| 1 | 73 | 84 | 90 | 95 | 100 |
| 2 | 55 | 76 | 87 | 97 | 100 |

What is claimed:

1. Method for producing antibiotic composites, said method comprising the following steps:
   a) providing a salt, which can be subjected to plastic deformation and which consists of:
      i) at least one cationic component of a protonated antibiotic base selected from the group consisting of aminoglycoside antibiotics, lincosamide antibiotics and tetracycline antibiotics; and
      ii) at least one anionic component selected from the group consisting of aliphatic carboxylates, alkyl sulfates, aryl sulfates, alkyl aryl sulfates cycloalkyl sulfates, alkyl cycloalkyl sulfates, alkyl sulfamates, cycloalkyl sulfamates, alkyl cycloalkyl sulfamates, aryl sulfamates, alkyl aryl sulfamates, alkyl sulfonates, fatty acid-2-sulfonates, aryl sulfonates, alkyl aryl sutfonates, cycloalkyl sulfonates, alkyl cycloalkyl sulfonates, alkyl-di-sulfates, cycloalkyl disulfates, alkyl disulfonates, cycloalkyl disulfonates, aryl disulfonates, alkyl aryl disulfonates, aryl trisulfonates and alkyl aryl trisulfonates;
   b) binding at least one member selected from the group consisting of inorganic composite components and organic composite components together with said salt form a composite; and
   c) molding the composite while adding water, wherein said molding comprises at least one of pressing, extrusion, rolling, calendaring and grinding.

2. Method for producing antibiotic composites according to claim 1, wherein the anionic component is selected from the group of alkyl sulfates.

3. Method for producing antibiotic composites in accordance with claim 1, wherein the anionic component is selected from the group of alkyl sulfonates, dodecyl sulfonate, hexadecyl sulfonate and octadecyl sulfonate.

4. Method for producing antibiotic composites in accordance with claim 1, wherein the anionic component is selected from aliphatic carboxylates, which contain 12 to 30 carbon atoms.

5. Method for producing antibiotic composites in accordance with claim 1, wherein the anionic component is selected from the group of aliphatic carboxylates palmitate, stearate and behenylate.

6. Method for producing antibiotic composites in accordance with claim 1, wherein the salt, which can be subjected to plastic deformation, is synthesized before the molding process.

7. Method for producing antibiotic composites in accordance with claim 1, wherein the salt, which can be subjected to plastic deformation, is formed during the molding process of the composite while introducing water into a mixture consisting of inorganic composite components, possibly organic composite components, one or more representatives from the aminoglycoside antibiotics and/or the lincosamide antibiotics and/or the tetracycline antibiotics, which exist in sulfate form, hydrochloride form, hydrobromide form and/or phosphate form, and one or more representatives from the alkyl sulfates, aryl sulfates, alkyl aryl sulfates, cycloalkyl sulfates, alkyl cycloalkyl sulfates, alkyl sulfamates, cycloalkyl sulfamates, alkyl cycloalkyl sulfamates, aryl sulfamates, alkyl aryl sulfamates, alkyl sulfonates, fatty acid-2-sulfonates, aryl sulfonates, alkyl aryl sulfonates, cycloalkyl sulfonates, alkyl cycloalkyl sulfonates, alkyl-disulfates, cycloalkyl disulfates, alkyl disulfonates, cycloalkyl disulfonates, aryl disulfonates, alkyl aryl disulfonates, aryl trisulfonates and alkyl aryl trisulfonates, which exist in sodium salt form and/or potassium salt form and/or in ammonium salt form and/or trialkyl ammonium salt form and/or in dialkyl ammonium salt form and/or in monoalkyl ammonium salt form and/or in triaryl ammonium salt form and/or in diaryl ammonium salt form and/or in aryl ammonium salt form and/or in alkyl diaryl ammonium salt form and/or in dialkyl aryl ammonium salt form and/or in tricycloalkyl ammonium salt form and/or in dicycloalkyl ammonium salt form and/or in monocycloalkyl ammonium salt form and/or in alkyl dicycloalkyl ammonium salt form and/or in dialkyl cycloalkyl ammonium salt form.

8. Method for producing antibiotic composites in accordance with claim 1, wherein the alkyl sulfates, aryl sulfates, alkyl aryl sulfates, cycloalkyl sulfates and alkyl cycloalkyl sulfates are sulphuric acid half esters.

9. Method for producing antibiotic composites in accordance with claim 1, wherein sodium dodecyl sulfate, sodium tetradecyl sulfate, sodium hexadecyl sulfate and sodium octadecyl sulfate are used as alkyl sulfates.

10. Method for producing antibiotic composites in accordance with claim 1, wherein sodium dodecyl sulfonate, sodium hexadecyl sulfonate and sodium octadecyl sulfonate are used as alkyl sulfonates.

11. Method for producing antibiotic composites in accordance with claim 1, wherein sodium dodecyl benzyl sulfonate is used as alkyl aryl sulfonate.

12. Method for producing antibiotic composites in accordance with claim 1, wherein one or more of calcium carbonate, magnesium carbonate, calcium hydroxide, magnesium hydroxide, magnesium oxide, calcium sulfate, calcium sulfate hemihydrate, calcium sulfate dihydrate, tricalcium phosphate, tetracalcium phosphate, calcium hydrogen phosphate, calcium hydrogen phosphate dihydrate, hydroxylapatite, fluorapatite, resorbable glass, resorbable glass ceramics and their mixtures are used as inorganic composite components.

13. Method for producing antibiotic composites in accordance with claim 1, wherein the inorganic composite components are used the form of powders and/or granulates.

14. Method for producing antibiotic composites in accordance with claim 1, wherein starch, cellulose, chitin, chitosan, gelatine, collagen, polymethacrylic acid ester, polyacrylic acid ester, polyvinyl alcohol, polyvinyl chloride, polyvinylidene chloride, polytetrafluorethylene, beeswax, carnauba wax, triglycerides and their blends are used as organic composite components.

15. Method for producing antibiotic composites in accordance with claim 1, wherein easily water-soluble antibiotics are used as organic composite components.

16. Method for producing antibiotic composites in accordance with claim 1, wherein the percentage by mass of salt that can be subjected to plastic deformation in the composites is between 0.1 and 98 mass percent.

17. Method for producing antibiotic composites in accordance with claim 1, wherein the composites are shaped into molded bodies, granulates and powders.

18. Method for producing antibiotic composites in accordance with claim 1, wherein the composites can be subjected to plastic deformation.

19. Method for producing antibiotic composites in accordance with claim 1, wherein the composites are in the form of pastes.

20. Method for producing antibiotic composites in accordance with claim 1, wherein the composites are applied onto resorbable implants and non-resorbable implants as coatings.

21. Method for producing antibiotic composites in accordance with claim 2, wherein the alkyl sulfates are selected from the group consisting of dodecyl sulfate, tetradecyl sulfate, hexadecyl sulfate, octadecyl sulfonate and docosanol sulfate.

* * * * *

UNITED STATES PATENT AND TRADEMARK OFFICE
CERTIFICATE OF CORRECTION

| | |
|---|---|
| PATENT NO. | : 6,942,877 B2 |
| APPLICATION NO. | : 10/100843 |
| DATED | : September 13, 2005 |
| INVENTOR(S) | : Vogt et al. |

It is certified that error appears in the above-identified patent and that said Letters Patent is hereby corrected as shown below:

Column 1, Line 33, "stored Through" should read -- stored through --

Column 1, Line 60, "a new ay" should read -- a new way --

Column 2, Line 20, "(α-hydroxy" should read -- α-hydroxy --

Column 7, Line 47, "aryl sulfates cycloalkyl" should read -- aryl sulfates, cycloalkyl --

Signed and Sealed this

Twenty-ninth Day of May, 2007

JON W. DUDAS
*Director of the United States Patent and Trademark Office*